US010596337B2

(12) United States Patent
Kamradt (10) Patent No.: US 10,596,337 B2
(45) Date of Patent: Mar. 24, 2020

(54) ADJUSTABLE TRACHEOSTOMA VALVE

(71) Applicant: Brian Kamradt, Indianapolis, IN (US)

(72) Inventor: Brian Kamradt, Indianapolis, IN (US)

(*) Notice: Subject to any disclaimer, the term of this patent is extended or adjusted under 35 U.S.C. 154(b) by 333 days.

(21) Appl. No.: 15/674,946

(22) Filed: Aug. 11, 2017

(65) Prior Publication Data

US 2018/0207382 A1 Jul. 26, 2018

Related U.S. Application Data

(60) Provisional application No. 62/499,397, filed on Jan. 25, 2017.

(51) Int. Cl.
*A61M 16/04* (2006.01)
*A61F 2/20* (2006.01)

(52) U.S. Cl.
CPC ......... *A61M 16/0468* (2013.01); *A61F 2/203* (2013.01); *A61M 16/0497* (2013.01)

(58) Field of Classification Search
CPC ............ A61M 16/048; A61M 16/0465; A61M 16/0497; A61M 16/20; A61M 39/22; A61F 2/03
USPC ..................................... 623/23.8; 128/207.16
See application file for complete search history.

(56) References Cited

U.S. PATENT DOCUMENTS

| 4,325,366 A * | 4/1982 | Tabor ................ A61M 16/0468 |
| | | 128/207.16 |
| 4,582,058 A | 4/1986 | Depel et al. |
| 4,971,054 A | 11/1990 | Andersson et al. |
| 5,059,208 A | 10/1991 | Coe et al. |
| 5,244,930 A * | 9/1993 | Trudell ............... A61M 1/1698 |
| | | 210/496 |
| 6,422,235 B1 | 7/2002 | Persson |
| 6,772,758 B2 | 8/2004 | Lambert |
| 6,921,417 B2 | 7/2005 | Persson |
| 7,025,784 B1 | 4/2006 | Blom et al. |
| 7,059,327 B2 | 6/2006 | Worthington |
| 7,370,654 B2 | 5/2008 | Persson |
| 8,505,537 B2 | 8/2013 | Persson |
| 8,678,005 B2 | 3/2014 | Dawson |
| 8,887,718 B2 | 11/2014 | Shikani et al. |
| 8,991,394 B2 | 3/2015 | Persson |
| 2002/0156527 A1 | 10/2002 | Persson |

(Continued)

FOREIGN PATENT DOCUMENTS

WO 2015067234 A2 5/2015
WO WO-2015067234 A2 * 5/2015

OTHER PUBLICATIONS

PCT International Search Report and Written Opinion for PCT International Patent Application No. PCT/US2018/014683, filed on Jan. 22, 2018, dated Mar. 29, 2018, 7 pages.

*Primary Examiner* — Kendra D Carter
*Assistant Examiner* — Suraj Kandalam
(74) *Attorney, Agent, or Firm* — Barnes & Thornburg LLP (57) ABSTRACT

An adjustable tracheostoma valve is disclosed. The adjustable tracheostoma valve includes a passageway for connecting the trachea with the surroundings. A valve disk is provided in the passageway. The disk is moveable to allow for inhalation and exhalation through the passageway and is configured to close in response to pressure to direct air to the patient's pharynx, esophagus, sinuses, and mouth for speech following surgical removal of the larynx.

21 Claims, 8 Drawing Sheets

(56) References Cited

U.S. PATENT DOCUMENTS

| | | | |
|---|---|---|---|
| 2003/0122095 A1* | 7/2003 | Wilson | A61B 5/0215 251/12 |
| 2004/0089291 A1 | 5/2004 | Persson | |
| 2015/0083119 A1 | 3/2015 | Persson | |
| 2015/0238718 A1* | 8/2015 | Schnell | A61F 2/20 128/202.27 |
| 2015/0273168 A1 | 10/2015 | Fahl | |
| 2015/0352349 A1* | 12/2015 | Carmody | A61M 5/165 137/544 |
| 2016/0256649 A1 | 9/2016 | Hesselmar | |
| 2016/0354569 A1 | 12/2016 | Fahl | |

\* cited by examiner

ADJUSTABLE TRACHEOSTOMA VALVE

This application claims priority under 35 U.S.C. § 119 to U.S. Patent App. Ser. No. 62/499,397, which was filed on Jan. 25, 2017 and is expressly incorporated herein by reference.

TECHNICAL FIELD

This disclosure relates to implantable devices for insertion to a tracheostoma and, more specifically, to devices adapted to control the flow of air through a tracheostoma.

BACKGROUND

Normal human speech utilizes the flow of expired air from the lungs up through the trachea and the larynx to vibrate the vocal cords in the larynx. If disease or injury requires the removal of the larynx, it becomes necessary to provide an alternative sound producing apparatus as a substitute for the vocal cords. Since the larynx normally blocks the lungs from contamination by esophageal contents, the surgeon must block the passage between the trachea and the pharyngeal esophagus. Consequently, during a typical laryngectomy, the surgeon creates an opening, or stoma, at the base of the patients neck to which the trachea is permanently diverted.

In one method of facilitating speech by the laryngectomee, the surgeon creates a new path for air to travel from the lungs and trachea to the pharyngeal esophagus. A voice prosthesis in the form of a cylindrically shaped, one-way valve may be inserted into this tracheoesophageal passageway. Various efforts have been made to provide a tracheal valve that will remain open to accommodate normal breathing, will close under speaking pressure so that exhalation products will pass into the pharynx for speech, and will open under higher pressure. Included are the techniques and devices illustrated and described in U.S. Pat. Nos. 4,582,058; 7,025,784; and 7,370,654. The disclosures of these references are hereby incorporated herein by reference. This listing is not intended as a representation that a complete search of all relevant prior art has been conducted, or that no better references than those listed exist.

To permit speech without manual occlusion of the stoma, a flange can be fastened over the tracheostoma and a valve inserted into the flange. This arrangement diverts the air flow from the trachea through the voice prosthesis. It is known in the prior art to provide tracheostoma valves with a movable diaphragm biased to an open position, as described in, for example, U.S. Pat. Nos. 5,059,208 and 7,370,654. Normal breathing pressures are insufficient to move the diaphragm to a closed position. Hence, the patient may readily inhale and exhale past the diaphragm.

Speech pressures, however, are initiated at somewhat higher levels. These higher pressures move the diaphragm to a closed position, blocking the free discharge of air to the atmosphere. The exhaled air can thus be diverted through the voice prostheses to the oral cavity where it produces sound that can be shaped into speech.

With different patients and changing exertion and respiration levels, no single diaphragm has the correct mechanical characteristics to work ideally in all situations. In the past, it has been necessary for the doctor to select a compromise valve diaphragm that works best for an individual patient in an average state of exertion.

SUMMARY

According to one aspect of the disclosure, an adjustable tracheostoma valve is disclosed. The adjustable tracheostoma valve includes a passageway for connecting the trachea with the surroundings, and a valve disk is provided in the passageway. The disk is attached to an air permeable membrane, which is configured to deflect under pressure to move the valve disk to a position that closes the passageway in response to pressure to direct air to the patient's pharynx, esophagus, sinuses, and mouth for speech following surgical removal of the larynx.

According to another aspect of the disclosure, a tracheostoma valve adapted to control the flow of air through a tracheostoma is disclosed. The valve comprises a first body including a passageway, and a second body movably coupled to the first body. The second body includes a rim surface surrounding a bore that is aligned with the passageway of the first body. The second body is movable relative to the first body to advance the bore toward and away from the passageway of the first body.

The valve also comprises an air permeable elastic membrane positioned in the passageway of the first body, and a disk having a first surface that is sized to cover the bore of the second body. The disk is attached to the air permeable elastic membrane. The air permeable elastic membrane is deflectable between a first position in which the first surface of the disk extends parallel to the rim surface of the second body and the disk is spaced apart from the bore of the second body to permit the passage of air through the bore and a second position in which the first surface of the disk engages the rim surface to cover the bore and prevent the passage of air through the bore. In some embodiments, the valve may further comprise a heat and moisture exchanger.

In some embodiments, the air permeable elastic membrane may extend outwardly from the passageway when located at the second position. In some embodiments, the second body may be pivotally coupled to the first body. Additionally, in some embodiments, the second body may be threaded onto the first body.

In some embodiments, the second body may comprise a plate including the rim surface and the bore, and a cylindrical barrel extending away from the plate and pivotally coupled to the first body. In some embodiments, the first body may comprise a base plate, an inner sleeve extending away from the base plate and including the passageway, and an outer sleeve extending away from the base plate and arranged concentrically with the inner sleeve such that an annular channel is defined between the inner sleeve and the outer sleeve. The annular channel may receive the cylindrical barrel of the second body.

In some embodiments, the cylindrical barrel may include a plurality of outer threads, and the outer sleeve may include a plurality of inner threads engaged with the outer threads of the cylindrical barrel.

Additionally, in some embodiments, the plate may include an annular grip sized to be grasped by a hand of a patient to move the second body between the first position and the second position.

In some embodiments, the first body may comprise a sleeve including the passageway, and a plurality of beams arranged concentrically with the sleeve, and the air permeable elastic membrane may include a plurality of arms. Each arm may be secured to an end of one of the plurality of beams.

In some embodiments, the air permeable elastic membrane may be formed of polyurethane open cell foam. Additionally, in some embodiments, the disk may be formed of polyurethane rubber.

According to another aspect, a tracheostoma valve adapted to control the flow of air through a tracheostoma comprises a housing including a posterior opening, and a cap including an anterior opening positioned opposite the posterior opening that is movably coupled to the housing. The valve further comprises a disk positioned between the posterior opening and the anterior opening, and an air permeable elastic membrane having a central section coupled to the disk and an outer edge coupled to the housing. The air permeable elastic membrane is deflectable under pressure to advance the disk over the anterior opening to prevent the passage of air through the anterior opening. When the cap is at a first position in the housing, the air permeable elastic membrane is configured to deflect a first amount when a first pressure is applied to the air permeable elastic membrane to advance the disk over the anterior opening to prevent the passage of air through the anterior opening. When the cap is at second position in the housing, the air permeable elastic membrane is configured to deflect a second amount when a second pressure is applied to the air permeable elastic membrane to advance the disk over the anterior opening to prevent the passage of air through the anterior opening. The second amount is greater than the first amount, and the second pressure being greater than the first pressure.

In some embodiments, the valve may further comprise a tape mount configured to be coupled to the housing. Additionally, in some embodiments, the cap may include a plate and a barrel extending from the plate, the barrel including an externally-threaded surface. The housing may include a sleeve having an internally-threaded surface that engages the externally-threaded surface of the cap.

In some embodiments, the housing may include a plurality of beams positioned concentrically with the sleeve. Each beam may have an end coupled to the air permeable elastic membrane.

In some embodiments, the housing may include an inner sleeve positioned concentrically with the sleeve, the inner sleeve including an inner rim coupled to the air permeable elastic membrane. Additionally, in some embodiments, the cap may be configured to be rotated in a first direction to move between the first position and the second position.

In some embodiments, the valve may further comprise a heat and moisture exchanger positioned in the housing between the anterior opening and the posterior opening.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been illustrated by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Figure 1:
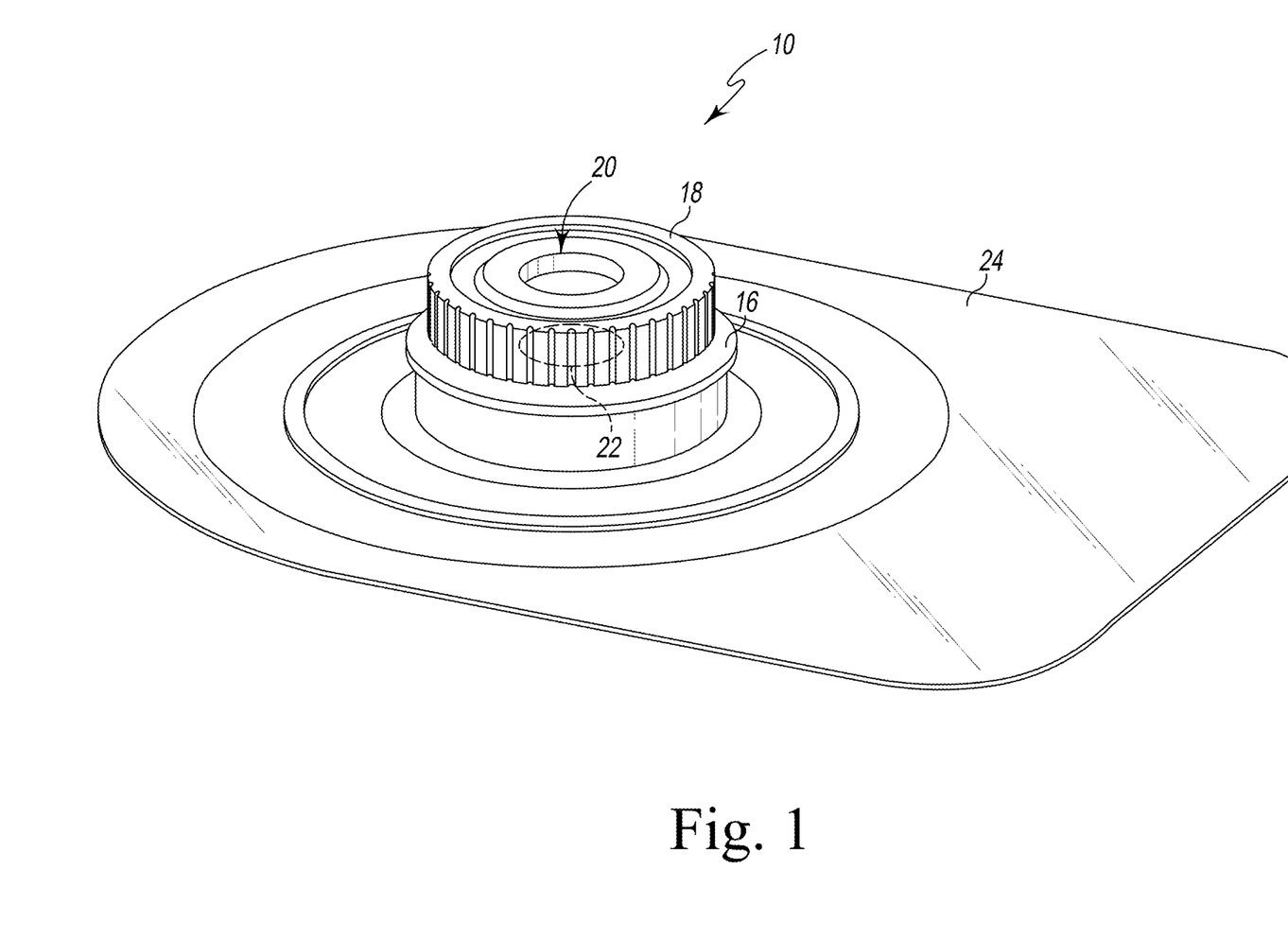
FIG. 1 as an illustration of a perspective view of an adjustable tracheostoma valve.

Referring now to FIG. 1, a tracheostoma valve 10 is shown. The tracheostoma valve 10 is configured to be positioned over a stoma 12 (see FIG. 6) that opens into a patient's trachea 14. The tracheostoma valve 10 includes a housing 16 and a cap 18 that is pivotally coupled to the housing 16. The housing 16 and the cap 18 cooperate to define a passage 20 for air to flow into and out of the patient's trachea 14 through the stoma 12. As described in greater detail below, the valve 10 also includes a valve member or disk 22 that is operable to close the passage 20 in response to pressure to direct air to the patient's pharynx, esophagus, sinuses, and mouth for speech following surgical removal of the larynx.

The housing 16 is attached to a tape mount 24, which may be attached to a patient's neck over the stoma 12. As shown in FIG. 1, the cap 18 is threaded into the housing 16 such that the cap 18 is operable to move relative to the housing 16 to increase or decrease the length of the passage 20 and thereby change the distance the disk 22 must travel to close the passage 20. It should be appreciated that in other embodiments the cap may be coupled to the housing via a combination of pins and slots, tapered surfaces, or other fastening means that permit the cap to move relative to the housing. In the illustrative embodiment, the housing 16 and the cap 18 are separately formed from a medical-grade plastic such as, for example, polypropylene. In other embodiments, the housing and/or cap may be formed from a silicone, metal, or other suitable material. The housing 16 and the cap 18 are illustratively formed as single, monolithic components. In other embodiments, they each may be formed from separate components that are later assembled.

Figure 2:
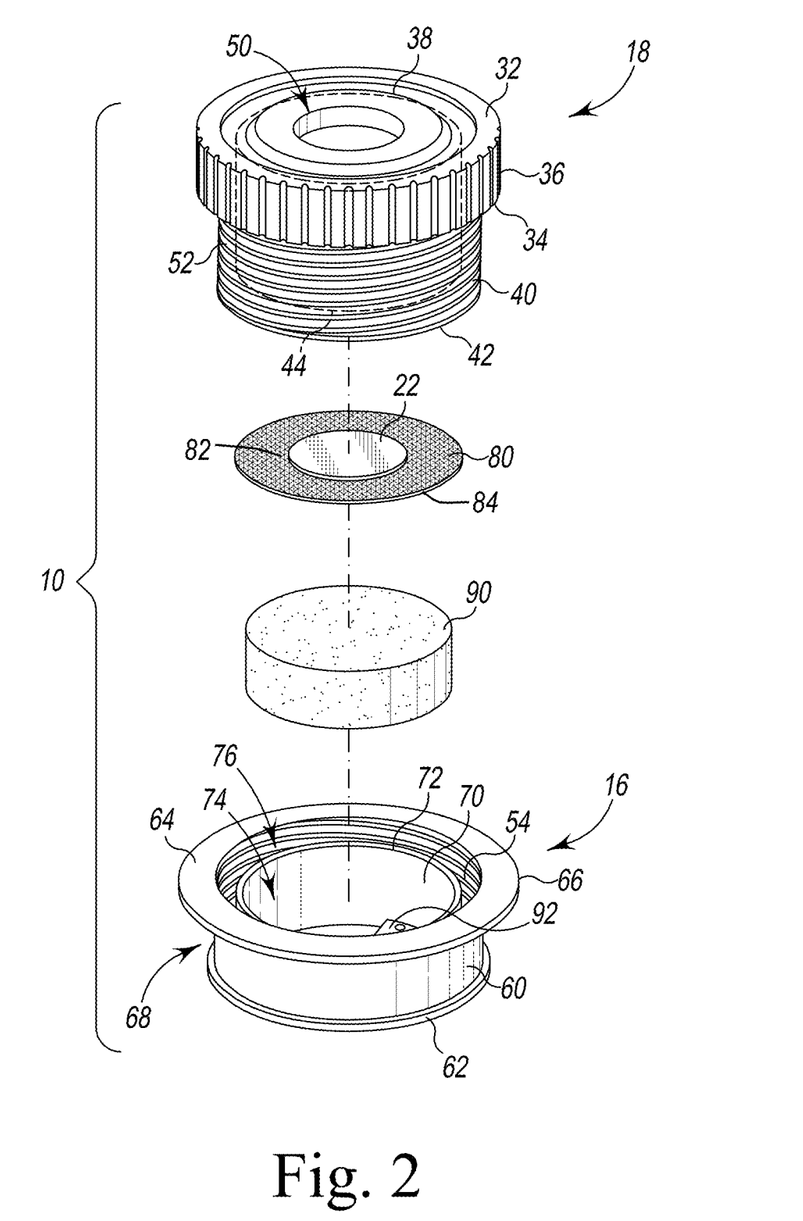
FIG. 2 is an exploded perspective view of the adjustable tracheostoma valve of FIG. 1.

Referring now to FIG. 2, the cap 18 includes a plate 30 having an anterior surface 32 and a posterior surface 34 positioned opposite the anterior surface 32. A rim wall 36 extends between the surfaces 32, 34. In the illustrative embodiment, the rim wall 36 is knurled to define an annular grip sized to be grasped by a hand of a patient to rotate the cap 18, as described in greater detail below. The plate 30 also includes an opening 38 that is defined in the anterior surface 32.

Figure 3:
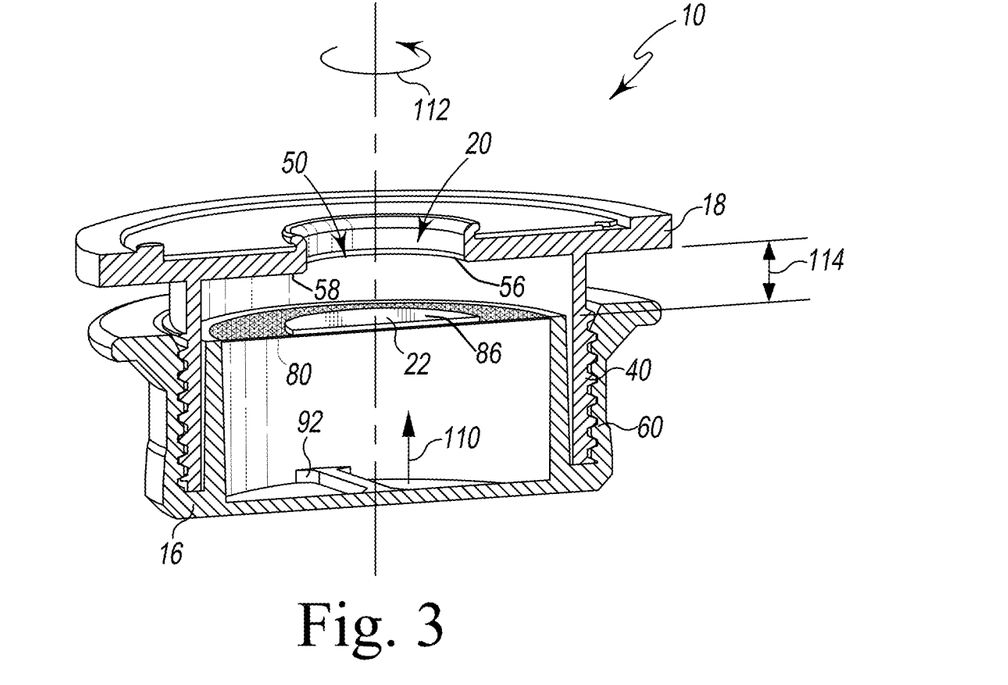
FIG. 3 is a cross-sectional perspective view of the adjustable tracheostoma valve of FIGS. 1-2 in one operational position with the heat moisture exchanger (HME) removed.

The cap 18 also includes a barrel 40 that extends from the posterior surface 34 of the plate 30 to a posterior end 42. The barrel 40 has an aperture 44 that extends inwardly from the end 42, and a bore 50 connects the aperture 44 to the opening 38 of the plate 30. In the illustrative embodiment, the barrel 40 is cylindrical and includes a threaded outer surface 52 that extends from the posterior surface 34 of the plate 30 to its posterior end 42. As described in greater detail below, the threaded outer surface 52 of the cap 18 is configured to engage the threaded inner surface 54 of the housing 16. As shown in FIG. 3, the bore 50 includes a posterior opening 56 that opens into the aperture 44. A rim surface 58 surrounds the opening 56 (and hence the bore 50). In the illustrative embodiment, the rim surface 58 forms the base of the aperture 44. In other embodiments, the rim surface 58 may include only the wall or surface that encloses the opening 56 and the bore 50.

As shown in FIG. 2, the threaded inner surface 54 of the housing 16 is included in an outer sleeve 60. The housing 16 also includes a posterior plate 62, and the outer sleeve 60 extends outwardly from the posterior plate 62 to an anterior end 64. An annular flange 66 extends outwardly from the anterior end 64 of the outer sleeve 60. In the illustrative embodiment, the flange 66 and the posterior plate 62 cooperate to define a groove 68 sized to receive a retaining tab (not shown) of the tape mount 24.

The housing 16 also includes an inner sleeve 70 that is arranged concentrically with the outer sleeve 60. The inner sleeve 70, like the outer sleeve 60, extends from the posterior plate 62 to an anterior rim 72 that surrounds an open passageway 74. As shown in FIG. 2, the passageway 74 extends through the housing 16 and includes a posterior opening in the plate 62. The inner sleeve 70 is spaced apart from the outer sleeve 60 such that an annular channel 76 is defined between the sleeves 60, 70. In the illustrative embodiment, the channel 76 is sized to receive the posterior end 42 of the barrel 40 of the cap 18 when the cap 18 is secured to the housing 16.

As described above, the trachestoma valve 10 includes a valve member or disk 22. The disk 22 is secured to an air permeable elastic membrane 80. As shown in FIG. 2, the elastic membrane 80 is circular-shaped, and the disk 22 is positioned in the approximate center of the circle. The elastic membrane 80 includes a central section 82 secured to the disk 22 and an outer circumferential edge or wall 84 that is attached to the anterior rim 72 of the inner sleeve 70. The elastic membrane 80 is formed of a polyurethane open cell foam that has a stretch ratio of 200-300% and a thickness in a range of 0.6 to 0.8 millimeters.

In the illustrative embodiment, the disk 22 is formed of a polyurethane rubber having a thickness of 0.8 millimeters and a durometer 60A. The disk 22 is secured to the central section 82 of the membrane 80 using a fastener such as, for example, glue that is cured using ultraviolet (UV) radiation. The disk 22 is circular in the illustrative embodiment and includes a generally planar surface 86 that is sized and shaped to completely cover the bore 50 of the cap 18. In use, the elastic membrane 80 is configured to deflect in response to pressure to position the surface 86 of the disk 22 in contact with the cap rim surface 58 and over the bore 50 defined in the cap 18 to close the passage 20 through the valve 10, as described in greater detail below.

In the illustrative embodiment, the valve 10 also includes a heat and moisture exchanger (HME) 90. One example of an HME is the Blom-Singer HME, which is commercially available from Inhealth Technologies. The exchanger 90 is sized to be positioned in the passageway 74 of the housing 16. As shown in FIG. 2, the housing 16 includes support beams 92 that cover the end of the passageway 74 to retain the exchanger 90 in the housing 16.

Figure 4:
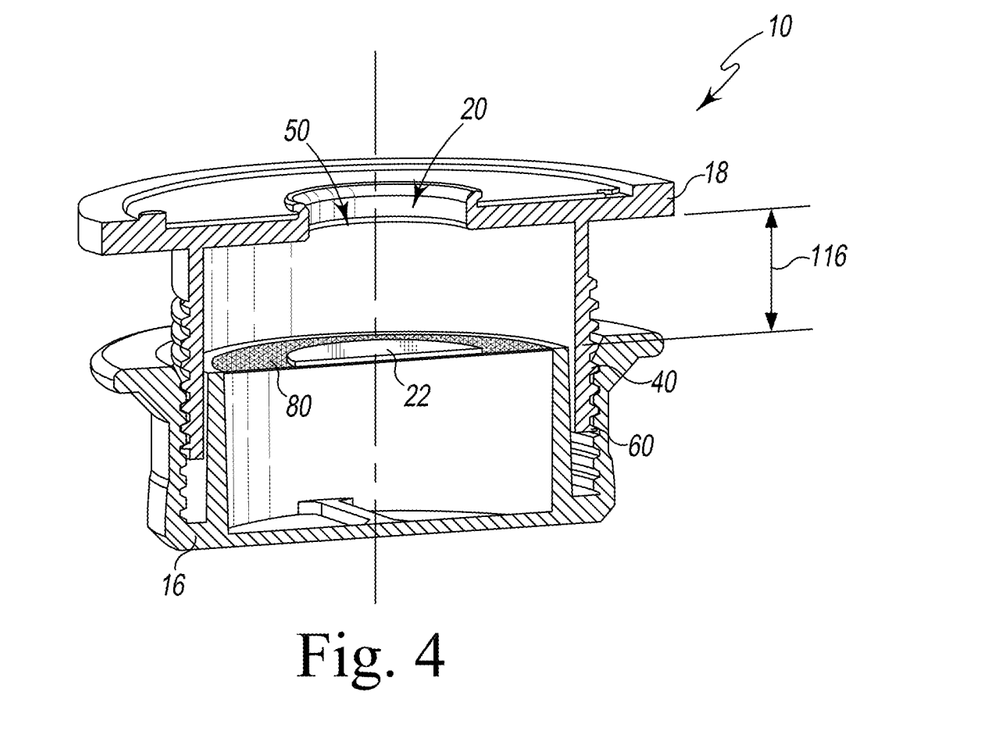
FIG. 4 is a view similar to FIG. 3 showing the adjustable tracheostoma valve in another operational position.
Figure 5:
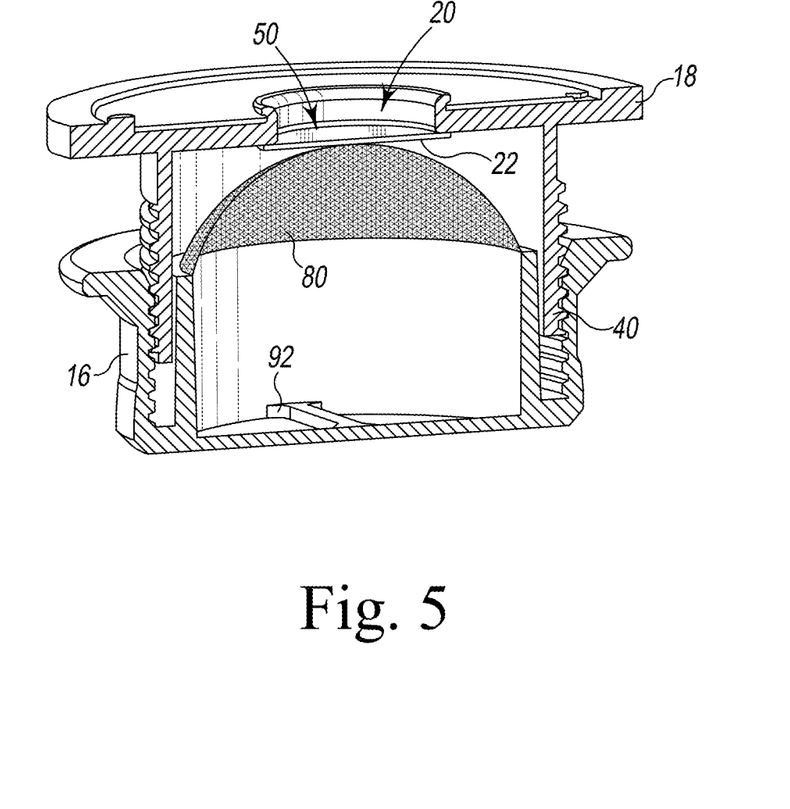
FIG. 5 is a view similar to FIGS. 3-4 showing the adjustable tracheostoma valve when actuated by pressure.
Figure 6:
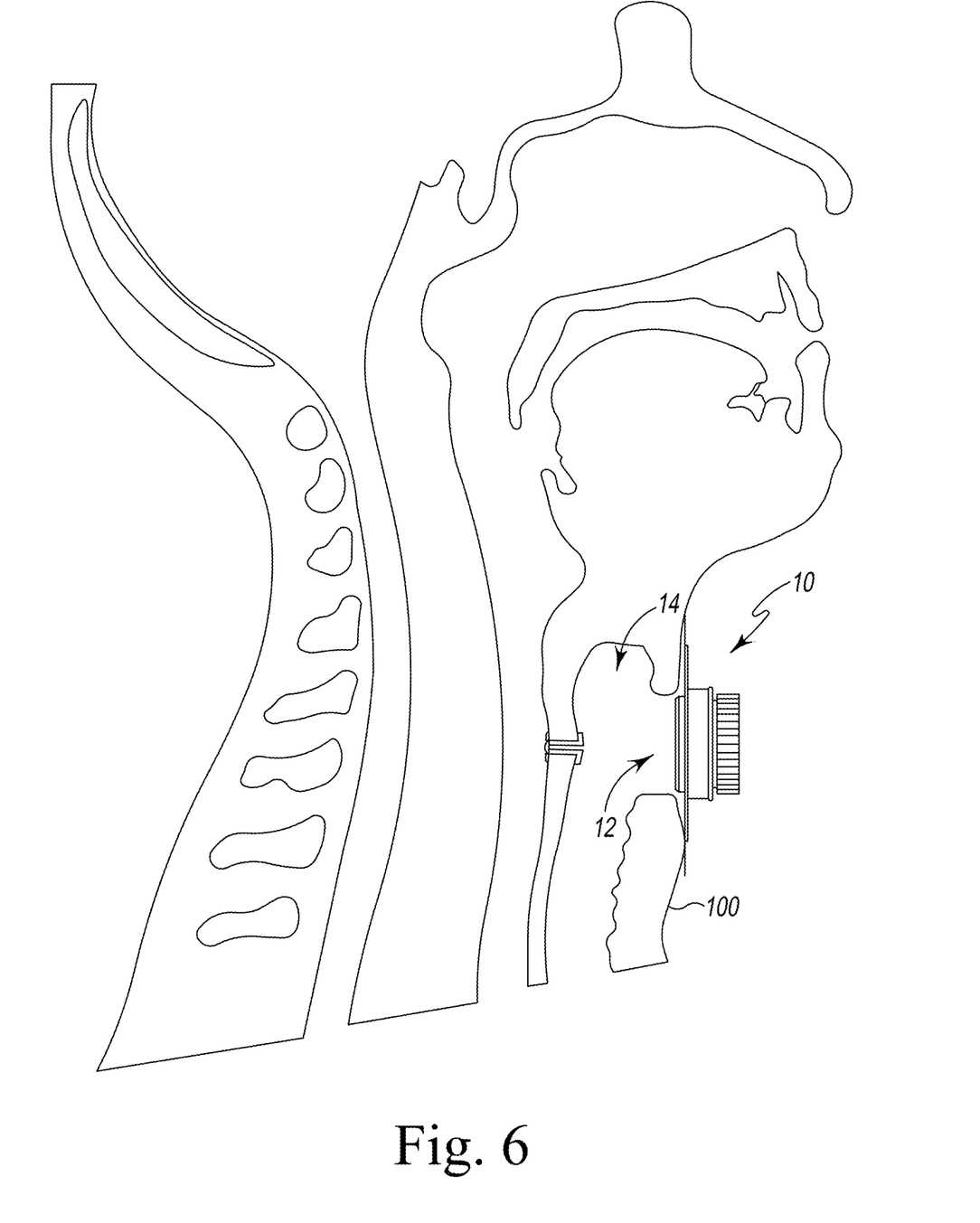
FIG. 6 is a side elevation view showing the adjustable tracheostoma valve positioned over a stoma of a patient.

Referring now to FIGS. 3-6, the adjustable valve 10 is shown in a number of operational positions. As shown in FIG. 6, when in use, the valve 10 is secured to the tape mount 24 and is positioned over a stoma 12 defined in a patient's neck 100. As described above, the stoma 12 opens into the patient's trachea 14. During inhalation, air enters the valve 10 through the bore 50 defined in the cap 18 and down the aperture 44 of the cap 18. The air passes through the membrane 80 and enters the passageway 74 defined in the inner sleeve 70 of the housing 16. The air move through the HME 90 and exits through the posterior opening of the passageway 74 into the trachea 14. As shown in FIG. 3, the surface 86 of the disk 22 is spaced apart from and extends parallel to the rim surface 58 of the cap 18 during inhalation.

During exhalation, air enters through the posterior opening of the passageway 74, as indicated by arrow 110 in FIG. 3. When the air exceeds a predetermined pressure, the membrane 80 is configured to deflect to advance the disk 22 anteriorly. As the disk 22 moves toward the bore 50, the surface 86 of the disk 22 remains generally parallel to the rim surface 58 of the cap 18. The disk 22 moves to engage the surface 86 of the disk 22 with the rim surface 58 of the cap 18 to cover the bore 50 and to close the passage 20 extending through the valve 10.

The patient or other user may adjust the pressure required to close the passage 20 by rotating the cap 18 relative to the housing 16. For example, when the cap 18 is rotated counterclockwise as indicated by arrow 112 in FIG. 3, the cap plate 30 (and hence the bore 50) is moved away from the housing 16, thereby increasing the length of the passage 20. As shown in FIGS. 3-4, the rim surface 58 surrounding the bore 50 may be initially separated from the surface 86 of the disk 22 by a distance 114; after rotating the cap 18, the rim surface 58 surrounding the bore 50 may be separated from the surface 86 of the disk 22 by a distance 116, thereby requiring the disk 22 to move farther within the passage 20 cover the bore 50, as shown in FIG. 5. As a result, greater pressure is required to cause the membrane 80 to deflect the distance 114 than to cause the membrane 80 to deflect the distance 116.

Figure 7:
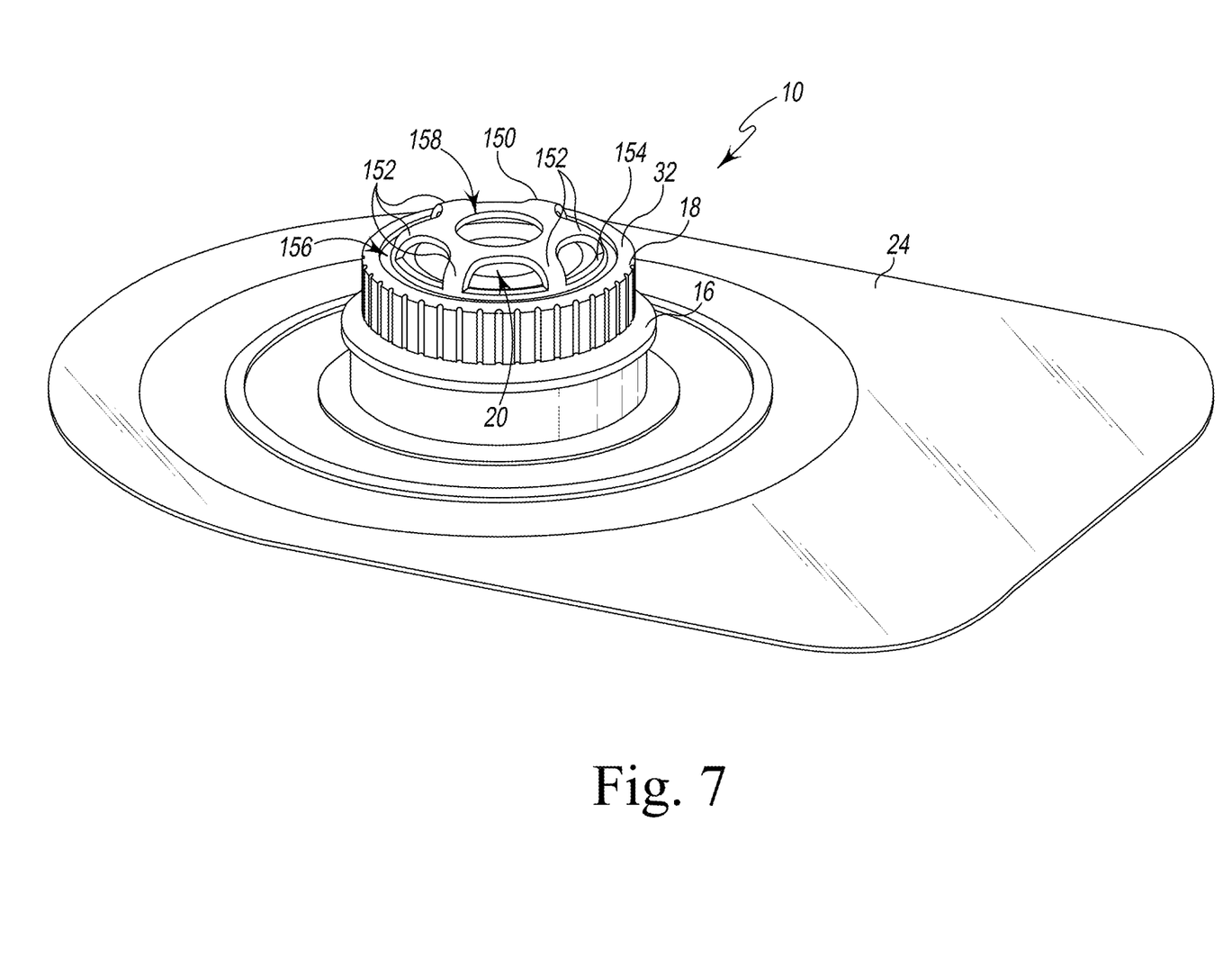
FIG. 7 is a perspective view of the adjustable tracheostoma valve of FIG. 1 with a cover.

Referring now to FIG. 7, the valve 10 is shown with a protective cover 150 attached to the cap 18. In the illustrative embodiment, the cover 150 includes a plurality of arms 152 extending from a base 154 sized to be positioned in a groove 156 defined in the anterior surface 32 of the cap 18. The cover 150 includes a plurality of openings 158 to permit air to move into and out of the passage 20 of the valve 10. In the illustrative embodiment, the cap 18 and the cover 150 are separately formed from a medical-grade plastic such as, for example, polypropylene. In other embodiments, the cap and cover may be illustratively formed as a single, monolithic component.

Figure 8:
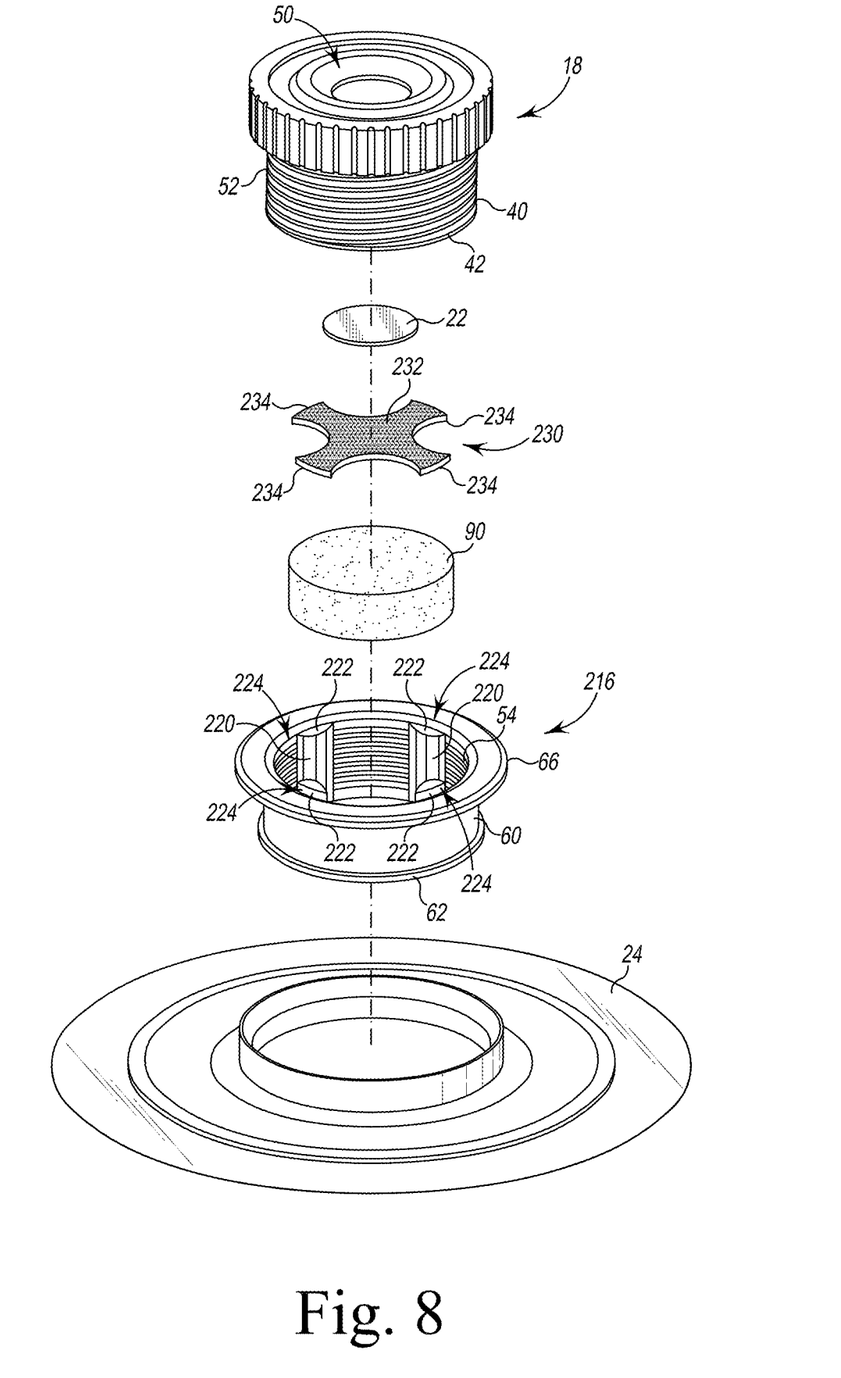
FIG. 8 is an exploded perspective view of another embodiment of an adjustable tracheostoma valve.

Referring now to FIG. 8, another embodiment of a valve 210 is shown. The embodiment of FIG. 8 includes a number of features that are identical to the embodiment described above in regard to FIGS. 1-6. For convenience, such features are identified with the same reference numbers. The valve 210, like the valve 10, includes a cap 18 that is threaded into a housing 216. The housing 216 is configured to be secured to a tape mount 24, as shown in FIG. 8.

The housing 216 includes a posterior plate 62 and an outer sleeve 60 that extends away from the posterior plate 62. The outer sleeve 60 includes a threaded inner surface 54 that is configured to be engaged with the threaded outer surface 52 of the cap 18. The housing 216 includes a plurality of beams 220 that extend away from the posterior plate 62. Each beam 220 includes a free anterior tip 222. In the illustrative embodiment, the beams 220 are arranged concentrically with the outer sleeve 60. The beams 220 are spaced apart from the threaded inner surface 54 of the sleeve 60 so that a plurality of channels 224 are defined between the beams 220 and the inner surface 54 of the sleeve 60. The channels 224 are sized to receive the posterior and 42 of the cap barrel 40.

The valve 210 also includes a disk 22 having a surface 86 that is sized to cover the rim surface 58 surrounding the bore 50 of the cap 18. The disk 22 is secured to an air permeable elastic membrane 230. The membrane 230 includes a central body 232 and a plurality of arms 234 that extend outwardly from the body 232. Each arm 234 has an outer edge that is secured to one of the anterior tips 222 of the beams 220. Similar to the membrane 80 described above in regard to FIGS. 1-6, the membrane 230 is configured to deflect under pressure to advance the disk 22 over the bore 52 close the passage 20 of the valve 210. The elastic membrane 230 is formed of a polyurethane open cell foam that has a stretch ratio of 200-300% and a thickness in a range of 0.6 to 0.8 millimeters. The disk 22 is secured to the membrane 230 using a fastener such as, for example, glue that is cured using ultraviolent (UV) radiation.

Figure 9:
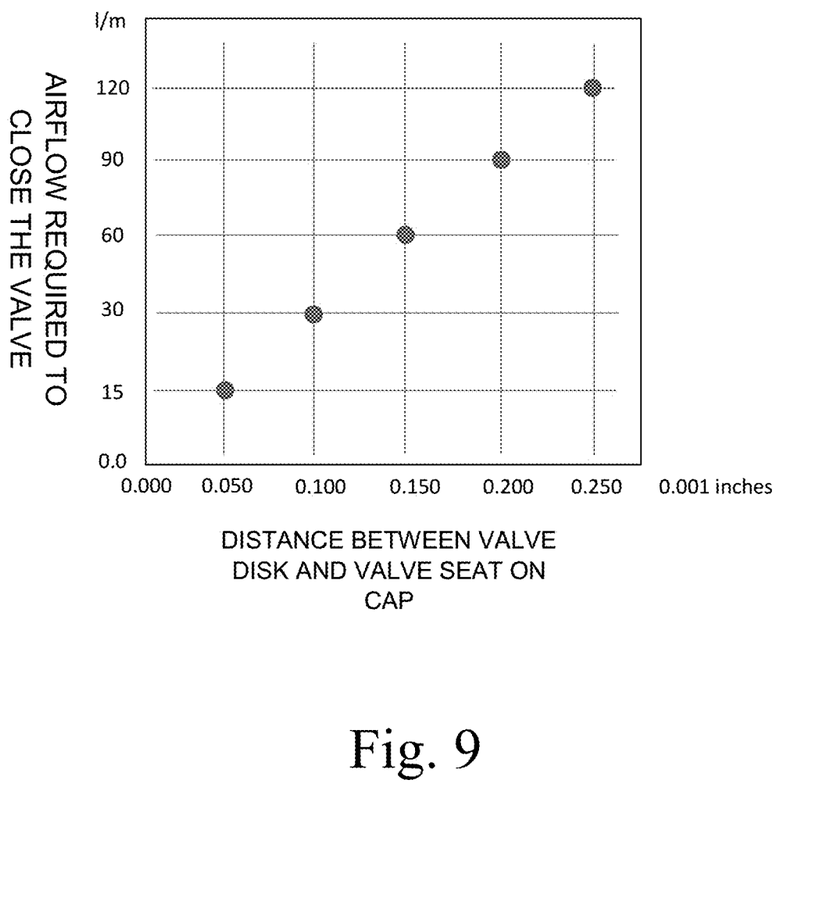
FIG. 9 is an illustration of a graph showing performance data of an embodiment of the adjustable tracheostoma valve.

Referring now to FIG. 9, a test was performed to measure the airflow at which the adjustable tracheostoma valve shown in FIGS. 1-5 closes (i.e., the disk engages the cap to cover the cap opening). The results show a flow range of 0 to 120 liters per minute (l/m) to close the valve, and that the airflow required to close the tracheostoma valve decreased linearly with the valve positions. In the illustrative embodiment, the valve will close in a range of 0.05 kPa and 0.5 kPa. The valve closes at 0.05 kPa when the distance initially separating the surface 86 of the disk 22 and the rim surface 58 surrounding the bore 50 is equal to 0.150 inches. The valve closes at 0.5 kPa when the distance initially separating the surface 86 of the disk 22 and the rim surface 58 surrounding the bore 50 is equal to 0.300 inches.

While the disclosure has been illustrated and described in detail in the drawings and foregoing description, such an illustration and description is to be considered as exemplary and not restrictive in character, it being understood that only illustrative embodiments have been illustrated and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

What is claimed is:

1. A tracheostoma valve adapted to control the flow of air through a tracheostoma comprising:
    a first body including a passageway,
    a second body movably coupled to the first body, the second body including a rim surface surrounding a bore that is aligned with the passageway of the first body,
    an air permeable elastic membrane positioned in the passageway of the first body, and
    a disk having a first surface that is sized to cover the bore of the second body, the disk being attached to the air permeable elastic membrane,
    wherein the second body is movable relative to the first body to advance the bore toward and away from the passageway of the first body, and
    wherein the air permeable elastic membrane is deflectable between a first position in which the disk is spaced apart from the bore of the second body to permit the passage of air through the bore and the first surface of the disk extends parallel to the rim surface of the second body and a second position in which the first surface of the disk engages the rim surface to cover the bore and prevent the passage of air through the bore.

2. The tracheostoma valve of claim 1, wherein the air permeable elastic membrane extends outwardly from the passageway when located at the second position.

3. The tracheostoma valve of claim 1, wherein the second body is pivotally coupled to the first body.

4. The tracheostoma valve of claim 3, wherein the second body is threaded onto the first body.

5. The tracheostoma valve of claim 3, wherein the second body comprises:
    a plate including the rim surface and the bore, and
    a cylindrical barrel extending away from the plate and pivotally coupled to the first body.

6. The tracheostoma valve of claim 5, wherein the first body comprises:
    a base plate,
    an inner sleeve extending away from the base plate and including the passageway, and
    an outer sleeve extending away from the base plate and arranged concentrically with the inner sleeve such that an annular channel is defined between the inner sleeve and the outer sleeve, the annular channel receiving the cylindrical barrel of the second body.

7. The tracheostoma valve of claim 6, wherein:
    the cylindrical barrel includes a plurality of outer threads, and
    the outer sleeve includes a plurality of inner threads engaged with the outer threads of the cylindrical barrel.

8. The tracheostoma valve of claim 5, wherein the plate includes an annular grip sized to be grasped by a hand of a patient to move the second body between the first position and the second position.

9. The tracheostoma valve of claim 5, wherein:
    the first body comprises a sleeve including the passageway, and a plurality of beams arranged concentrically with the sleeve, and
    the air permeable elastic membrane includes a plurality of arms, each arm being secured to an end of one of the plurality of beams.

10. The tracheostoma valve of claim 1, further comprising a heat and moisture exchanger.

11. The tracheostoma valve of claim 1, wherein the air permeable elastic membrane is formed of polyurethane open cell foam.

12. The tracheostoma valve of claim 1, wherein the disk is formed of polyurethane rubber.

13. A tracheostoma valve adapted to control the flow of air through a tracheostoma comprising:
    a housing including a posterior opening,
    a cap movably coupled to the housing, the cap including an anterior opening positioned opposite the posterior opening,
    a disk positioned between the posterior opening and the anterior opening, and
    an air permeable elastic membrane having a central section coupled to the disk and an outer edge coupled to the housing, the air permeable elastic membrane being deflectable under pressure to advance the disk over the anterior opening to prevent the passage of air through the anterior opening,
    wherein when the cap is at a first position in the housing, the air permeable elastic membrane is configured to deflect a first amount when a first pressure is applied to the air permeable elastic membrane to advance the disk over the anterior opening to prevent the passage of air through the anterior opening, and wherein when the cap is at second position in the housing, the air permeable elastic membrane is configured to deflect a second amount when a second pressure is applied to the air permeable elastic membrane to advance the disk over the anterior opening to prevent the passage of air through the anterior opening, the second amount being greater than the first amount, and the second pressure being greater than the first pressure.

14. The tracheostoma valve of claim 13, further comprising a tape mount configured to be coupled to the housing.

15. The tracheostoma valve of claim 13, wherein:
the cap includes a plate and a barrel extending from the plate, the barrel including an externally-threaded surface, and
the housing includes a sleeve having an internally-threaded surface that engages the externally-threaded surface of the cap.

16. The tracheostoma valve of claim 15, wherein the housing includes a plurality of beams positioned concentrically with the sleeve, each beam having an end coupled to the air permeable elastic membrane.

17. The tracheostoma valve of claim 15, wherein the housing includes an inner sleeve positioned concentrically with the sleeve, the inner sleeve including an inner rim coupled to the air permeable elastic membrane.

18. The tracheostoma valve of claim 13, wherein the cap is configured to be rotated in a first direction to move between the first position and the second position.

19. The tracheostoma valve of claim 13, wherein the air permeable elastic membrane is formed of polyurethane open cell foam.

20. The tracheostoma valve of claim 13, further comprising a heat and moisture exchanger positioned in the housing between the anterior opening and the posterior opening.

21. A tracheostoma valve adapted to control the flow of air through a tracheostoma comprising:
a housing including a posterior opening,
a cap movably coupled to the housing, the cap including an anterior opening positioned opposite the posterior opening,
a disk positioned between the posterior opening and the anterior opening, and
an elastic membrane having a central section coupled to the disk and an outer edge coupled to the housing, the elastic membrane being deflectable under pressure to advance the disk over the anterior opening to prevent the passage of air through the anterior opening,
wherein when the cap is at a first position in the housing, the elastic membrane is configured to deflect a first amount when a first pressure is applied to the elastic membrane to advance the disk over the anterior opening to prevent the passage of air through the anterior opening, and
wherein when the cap is at second position in the housing, the elastic membrane is configured to deflect a second amount when a second pressure is applied to the elastic membrane to advance the disk over the anterior opening to prevent the passage of air through the anterior opening, the second amount being greater than the first amount, and the second pressure being greater than the first pressure.

* * * * *